United States Patent [19]

Palepu et al.

[11] Patent Number: 4,963,551
[45] Date of Patent: Oct. 16, 1990

[54] STABLE LYOPHILIZED FORM OF (S)-(+)-BIS-4,4'-(1-METHYL-1,2-ETHANEDIYL)2,6-PIPERAZINEDIONE AND SOLUTIONS THEREOF

[75] Inventors: Nagesh R. Palepu; Joyce W. Martin, both of Franklin County, Ohio

[73] Assignee: Erbamont Inc., Dublin, Ohio

[21] Appl. No.: 463,844

[22] Filed: Jan. 12, 1990

Related U.S. Application Data

[63] Continuation of Ser. No. 136,036, Dec. 21, 1987, abandoned.

[51] Int. Cl.$^5$ .............................................. A61K 31/495
[52] U.S. Cl. ..................................... 514/252; 514/970; 544/357
[58] Field of Search ................. 514/252, 970; 544/357

[56] References Cited

U.S. PATENT DOCUMENTS

| | | | |
|---|---|---|---|
| 3,196,153 | 7/1965 | Dazzi | 544/357 |
| 4,275,063 | 6/1981 | Creighton | 514/252 |
| 4,764,614 | 8/1988 | Miller | 544/357 |

FOREIGN PATENT DOCUMENTS 927423  5/1963  United Kingdom ................ 544/357

OTHER PUBLICATIONS

Repta et al., *J. Pharm. Sci.*, 1976, 65(2), 238–42.

*Primary Examiner*—Mark L. Bell
*Assistant Examiner*—David M. Brunsman
*Attorney, Agent, or Firm*—Thompson, Hine and Flory

[57] ABSTRACT

The present invention is directed to a stable, rapidly soluble lyophilized injectable composition containing up to about 6% moisture and capable of being stored at room temperature comprising the hydrochloric or sulfate salt of a compound selected from the group consisting of (S)-(+)-bis-4,4'-(1-methyl-1,2-ethanediyl)2,6-piperazinedione and (R)-(−)-bis-4,4'-(1-methyl-1,2-ethanediyl)2,6-piperazinedione; wherein said lyophilized composition is prepared from a bulk solution comprising from about 25 mg/mL to about 40 mg/mL of said compound dissolved in a hydrochloric acid or sulfuric acid; wherein the pH of said bulk solution is from about 1.0 to about 2.0. The invention is further directed to an isotonic solution which is formed upon reconstitution of the lyophilizate of the invention with a pharmaceutically acceptable diluent.

15 Claims, No Drawings

STABLE LYOPHILIZED FORM OF (S)-(+)-BIS-4,4'-(1-METHYL-1,2-ETHANEDIYL)2,6-PIPERAZINEDIONE AND SOLUTIONS THEREOF

This is a continuation of Ser. No. 136,036, filed 12-21-87, now abandoned.

BACKGROUND OF THE INVENTION

Doxorubicin hydrochloride (HCl) is an antineoplastic agent which is highly effective and has a broad spectrum of activity against many forms of cancer. It is the most widely used antineoplastic in many countries including the USA and Western Europe. Doxorubicin HCl is often included in multi-drug regimens and has become the mainstay of chemotherapy. This drug is marketed in North America by Adria Laboratories, Division of Erbamont Inc., under the trademark "Adriamycin."

A serious side effect which may result from cumulative doses of doxorubicin HCl exceeding 550 mg/m$^2$ is irreversible myocardial toxicity with delayed congestive heart failure often unresponsive to cardiac support therapy. This toxicity may occur at lower cumulative doses in patients with prior mediastinal irradiation or on concurrent cyclophosphamide therapy.

Clinical studies have shown that the compound (S)-(+)-bis-4,4'-(1-methyl-1,2-ethanediyl)2,6-piperazinedione (ADR-529, formerly referred to as ICRF-187), is a cardioprotective agent which can reduce or prevent the myocardial toxicity resulting from administration of doxorubicin HCl. (See Green et al, *PROC. ASCO*, 1987 6:28). Other highly desirable properties of ADR-529 are activity as a divalent cation chelating agent, sensitizer to ionizing radiation, anti-metastic agent and synergistic agent with anthracyclines in terms of anti-tumor effect.

ADR-529 is prepared as a lyophilized white powder according to conventional lyophilization techniques well known in the art. Briefly, this process involves the steps of preparing an aqueous solution of ADR-529, filling this solution into glass vials and thereafter sublimating the water under vacuum in a lyophilizer. The lyophilizate is reconstituted with a suitable pharmaceutically acceptable diluent, e.g., 0.9% sodium chloride solution to give a solution, which may thereafter be intravenously administered to a patient.

The present recommended clinical dose of ADR-529 is 1 g/m$^2$ of body surface. Currently, depending on the body weight of the patient, the clinician must reconstitute 4 to 8 vials containing 250 mg of lyophilized ADR-529 per vial.

The contents of the reconstituted vials are pooled into an IV bag and the pooled contents are administered to a patient by infusion over 15 minutes. It can be appreciated that it would be highly desireable to minimize the number of vials to be reconstituted and to reduce the possibility of cross contamination of the final solution due to pooling of the reconstituted portions.

The largest standard vial size which is conventionally used in the lyophilizer is 100 cc. Generally, the solution to be lyophilized is added to the vial so as to occupy about one-half of the volume of the vial. If the vial is filled any fuller, it is difficult to establish steady state vapor pressure and as a result, the lyophilization cycle is slowed significantly. Also, there will not be enough room for the solution to expand in the vial upon freezing and, when the frozen solution expands, the vial may break. The breakage is high for large volume vials because they are weak.

The solubility of ADR-529 in water is 10 mg/mL at 25° C. Accordingly, one (1) gram of ADR-529 will not dissolve in 50 mL of water which is about the maximum amount of solution which should be added to a 100 cc vial for the subsequent lyophilization process.

Of course, a vial with a nominal fill volume of 200–220 mL could be used. There are however, significant disadvantages to using a larger vial size. Most vial filling equipment is designed to fill conventional 100 cc vials. Development of alternative equipment would be both time consuming and expensive. Further, the lyophilization cycle will take longer because larger volumes of liquid must be removed plus fewer vials can be processed during the lyophilization cycle since the larger vials occupy more space in the lyophilizer.

It can be appreciated that it would be highly desirable to be able to increase the solubility of ADR-529 in water so as to get one gram of ADR-529 dissolved in 50 mL of water. This would allow for subsequent lyophilization in 100 cc vials using conventional filling equipment and lyophilization techniques.

Another disadvantage of conventional lyophilized ADR-529 is that the lyophilized material has a tendency to convert to the crystalline form upon storage at ambient temperature. The presence of even a small amount of crystals in the lyophilizate greatly increases the dissolution rate (i.e., reconstitution time) of the lyophilizate from about 30 sec. to about 15 min. The conversion of ADR-529 from the amorphous to the crystalline form appears to be related to the moisture in the lyophilizate. The presence of greater then 2% moisture in the lyophilizate will result in formation of crystals. To prevent crystal formation, conventional lyophilized vials of ADR-529 should be stored under refrigeration.

It is therefore an object of the invention to prepare a lyophilizate of ADR-529 which is stable at room temperature for about 2 years and which has a dissolution time of about 1 sec. to about 5 sec. when reconstituted with a pharmaceutically acceptable diluent so as to produce an isotonic solution suitable for intravenous injection into a patient.

It is yet another object of the invention to prepare a lyophilizate of ADR-529 using conventional 100 cc vials as well as conventional filling and lyophilization equipment.

Yet, a further embodiment of the invention is directed to an injectable isotonic solution having a pH of about 3.0 to about 6.0, which contains about 10 mg/mL of the active drug substance (ADR-529).

SUMMARY OF THE INVENTION

The present invention is directed to a stable, rapidly soluble lyophilized injectable composition containing up to about 6% moisture and capable of being stored at room temperature which comprises the hydrochloric acid or sulfuric acid salt of a compound selected from the group consisting of (S)-(+)-bis-4,4'-(1-methyl-1,2e-thanediyl)2,6-piperazinedione and (R)-(-)-bis-4,4-(methyl-1,2-ethanediyl)2,6-piperazinedione; wherein said lyophilized composition is prepared from a bulk solution comprising from about 20 mg/mL to about 40 mg/mL of said compound dissolved in hydrochloric acid or sulfuric acid and wherein the pH of said bulk solution is from about 1.0 to about 2.0.

The present invention is further directed to an isotonic solution which is suitable for intravenous adminstration to a patient in need of treatment having a pH of from about 3.0 to about 6.0, wherein said isotonic solution is formed by reconstituting the lyophilizate described above with a quantity of a pharmaceutically acceptable diluent sufficient tO prOduce said isotOnic sOlutiOn.

DETAILED DESCRIPTION OF INVENTION

The invention is directed to a stable, rapidly soluble lyophilized injectable composition containing up to about 6% moisture and capable of being stored at room temperature which comprises the hydrochloric acid or sulfuric acid salt of a compound selected from the group consisting of (S)-(+)-bis-4,4'-(1-methyl-1,2-ethanediyl)2,6piperazinedione and (R)-(-)-bis-4,4'-(1-methyl-1,2ethanediyl)2,6-piperazinedione; wherein said lyophilized composition is prepared from a bulk solution comprising from about 20 mg/mL to about 40 mg/mL of said compound dissolved in hydrochloric or sulfuric acid and wherein the pH of said bulk solution is from about 1.0 to about 2.0.

The invention is further directed to an isotonic solution suitable for intravenous administration to a patient in need of treatment which has a pH of from about 3.0 to about 6.0 wherein said isotonic solution is formed by reconstituting a lyophilizate with a quantity of a pharmaceutically acceptable diluent; wherein said lyophiiizate is a stable, rapidly soluble lyophilized injectable composition containing up to about 6% moisture and capable of being stored at room temperature which comprises the hydrochloric acid or sulfuric acid salt of a compound selected from the group consisting of (S)-(+)-bis-4,4'-(1-methyl-1,2-ethanediyl)2,6-piperazinedione and (R)-(-)-bis-4,4'-(1-methyl-1,2-ethanediyl)2,6piperazinedione wherein said lyophilized composition is prepared from a bulk solution comprising from about 20 mg/mL to about 40 mg/mL of said compound dissolved in hydrochloric acid or sulfuric acid and wherein the pH of said bulk solution is from about 1.0 to about 2.0.

Although the compound (S)-(+)-bis-4,4'-(1-methyl1,2-ethanediyl)2,6-piperazinedione, i.e., ADR-529 is preferred for use herein, the present invention is equally applicable to its isomer, i.e., (R)-(-)-bis-4,4'-(1-methyl1,2-ethanediyl)2,6-piperazinedione and a lyophilized injectable composition and an isotonic solution containing this isomer is within the scope of the invention described herein. The racemic mixture is not contemplated for use herein.

The preparation of (S)-(+)-bis-4,4'-(1-methyl-1,2ethanediyl)2,6-piperazinedione and (R)-(-)-bis-4,4'-(1-methyl-1,2-ethanediyl)2,6-piperazinedione is described in U.S. Pat No. 3,941,790 and U.S. Pat. No. 4,275,063 describes a pharmaceutical composition useful for aiding regression and palliation of sarcoma, lymphosarcoma and leukemia in animals containing these compounds as the active agent.

As used herein the term "isotonic" is understood to have its commonly understood meaning and is "a solution that has the same osmotic pressure as blood serum."

It is possible to reconstitute the lyophilizate of the invention with a pharmaceutically acceptable diluent so as to produce a slightly hypertonic solution, i.e., a solution having a slightly higher osmotic pressure than blood. Such solutions may be injected into the veins of patients and are contemplated within the scope of the isotonic solution of the present invention.

The isotonic solution of the invention is "suitable for intravenous bolus administration to a patient". The term "bolus injection" (also referred to as "IV push") refers to the rapid injection of the solution into the vein of a patient being treated as opposed to the slow drip of the solution into the vein.

As used herein the term "reconstitution", "reconstituting", "reconstituted" and the like refers to the process of adding a pharmaceutically acceptable diluent or solvent to a lyophilizate of the strong acid salt of (S)(+)-bis-4,4'-(1-methyl-1,2-ethanediy1)2,6-piperazinedione or (R)-(-)-bis-4,4'-(1-methyl-1,2-ethanediyl)2,-6piperazinedione so as to form an isotonic solution. The pharmaceutically acceptable diluent should be choosen so that the resulting pH of the isotonic solution of the invention is from about 3.0 to about 6.0 and preferably from about 3.5 to about 5.0 and more preferably about 4.5 to about 5.5.

As used herein the term "pharmaceutically acceptable diluent" refers to an aqueous solvent which is compatible with human blood serum and which may be injected into the veins or arteries of said human without producing a diliterous effect on the patient. Suitable diluents are described in *The United States Pharmacopeia Twenty-First Revision*; The National Formulary Sixteenth Revision, 1985; United States Pharmacopeial Convention, Inc., 12601 Twinbrook Parkway, Rockville, MD 20852. Suitable pharmaceutically acceptable diluents are for example sodium hydroxide, potassium hydroxide, tri-basic phosphate, dibasic phosphate, 1-lysine and 1-arganine. Especially preferred for use herein is sodium hydroxide containing sufficient sodium chloride so as to make the reconstituted lyophilizate solution isotonic.

As used herein the terms "active drug substance," or "ADS" refers to the compound (S)-(+)-bis-4,4'-(1-methyl1,2-ethandiyl)2,6-piperazinedione or the compound (R)-(-)-bis-4,4'-(1-methyl-1,2-ethanediyl)2,6-piperazined The term "lyophilizate" refers to the dry form of the "bulk solution" of the strong acid salt of (S)-(+)-bis4,4'-(1-methyl-1,2-ethanediyl)2,6-piperazinedione or (R)-(-)-bis-4,4'-(1-methyl-1,2-ethanediyl)2,-piperazinedione which has been prepared by rapid freezing and dehydration in the frozen state under high vacuum using conventional procedures well known in the pharmaceutical manufacturing art.

If the lyophilizate of the invention is reconstituted with sterile water or sterile saline, the pH of the resulting solution is about 2. A solution having a pH of 2 is not acceptable for intravenous injection into a patient, it is necessary to reconstitute the lyophilizate of the invention with a pharmaceutically acceptable basic solution to produce a pH in the range of 4.5–6.0. The pH of the reconstituted solution should be kept in this range as (S)-(+)-bis-4,4'-(1-methyl-1,2-ethanediyl)2,6piperazinedione and its R-isomer chemically degrade at pH's above 7.0.

The term "shelf-stable" or "stable" as used herein means that the "finished dosage form" of the lyophilizate of the present invention can be stored for extended periods of time, on the order of at least 1½ to 2 years, at room temperature without appreciable decomposition of the active drug substance or the formation of crystals of the active drug substance.

The term "finished doseage form" refers to the lyophilizate of the invention contained in a glass or plastic vial which has an appropriate container closure system.

For the requirements for such containers and closure systems. See, USP XXI, pp. 1233-1240 and pp. 1198-1199.

The acids which are suitable for use to prepare the active drug substance are hydrochloric acid which forms the hydrochloride salt and sulfuric acid which forms the salt and sulfuric acid, which forms the sulfate salt.

The hydrochloride salt of (S)-(+)-bis-4,4'-(1-methyl-1,2-ethanediyl)2,6-piperazinedione is unique in that it is significantly (3-3½ times) more soluble than amorphous (S)-(+)-bis-4,4'-(1-methyl-1,2-ethanediyl)2,6piperazinedione.

As used herein the term "bulk solution" refers to an aqueous solution of the acid salt of (S)-(+)-bis-4,4'-(1-methyl-1,2-ethanediyl)2,6-piperazinedione or (R)-(-)-4,4'-(1-methyl-1,2-ethanediyl)2,6-piperazinedione formed by dissolving from about 25 mg/mL of the active drug substance in 50 mL of 0.01 N HCl or $H_2SO_4$ at room temperature. The final pH of the bulk solution will be about 2.0. Normally, 1 the solubility of the active drug substance in water at 25° C. is 10-12 mg/mL. By lowering the pH of the solution to about 2.0 the solubility of the active drug substance is increased to about 35 mg/mL which allows one to prepare a bulk solution containing a concentrated amount of said active drug substance.

The isotonic solution of the invention is prepared as follows the bulk solution is prepared, filled into glass vials and the vials are partially stoppered. Thereafter, the vials are placed in a lyophilizer and the contents are lyophilized. The lyophilizate is reconstituted using a pharmaceutically acceptable diluent.

The following example illustrates the invention in further detail. This example is merely illustrative and is not meant to be limiting of the scope of the invention.

EXAMPLE 1

Preparation of Lyophilizate of HCl Salt of (S)-(+)-Bis-4,4'-(1-Methyl-1,2-Ethanediyl)2,6-Piperazinedione A quantity of (S)-(+)-bis-4,4'-(1-methyl-1,2ethanediyl)2,6-piperazinedione is dissolved in 0.10 N HCl to give a bulk solution having a pH of 2.0 and containing 25 mg/mL (S)-(+)-bis-4,4'-(1-methyl-1,2-ethanediyl)2,6piperazinedione as the hydrochloride salt. The bulk solution was thereafter sterilized by aseptic filtration according to conventional procedures used in the pharmaceutical industry. The bulk solution was filled into USP Type 1 flint glass vials having a fill capacity of 100 cc and the vials were partially stoppered with 20 mm siliconized lyophilization stoppers. Conventional aseptic techniques were followed during the filling and stoppering procedure. The contents of the stoppered vials are thereafter lyophilized using a Virtis Sublimator Model 10-MRPC with Free Zemobile II attachment manufactured by The Virtis Company, Garden City, N.Y. Aseptic techniques were followed throughout the lyophilization process. Visual observation of the lyophilizate cakes revealed that the cakes appeared slightly pink and glossy with cracks. The cakes contained about 6.0% moisture. Table 1 summarizes the lyophilization cycles.

TABLE 1

| Cycle Summary | Details of Lyophilization | | Time of Cycle (hr.) |
|---|---|---|---|
| | Shelf. Temp. °C. | Vial Temp. °C. | |
| Insert Samples | +25→−38 | +25→−32 | 3 |
| Vacuum On | −38 | −32→−12 | 16 |
| Shelves To | | | |
| −15 | −38→−15 | −12→0 | 4.5 |
| −10 | −15→−12 | −0 | 0.5 |
| −5 | −12→−7 | 0→+3 | 0.5 |
| 0 | −7→−1 | +3 | 0.5 |
| +10 | +1→+8 | +3→+10 | 1 |
| +15 | +8→+13 | +10→+20 | 17 |
| +30 | +13→28 | +20→+27 | 3 |

The lyophilizate of the present invention is stable upon storage at room temperature. On the other hand, conventionally lyophilized (S)-(+)-bis-4,4'-(1-methyl-1,2ethanediyl)2,6-piperazinedione suffers from the disadvantage that it converts from the amorphous state to the crystalline form in the presence of greater than 2% moisture upon storage at room temperature. As a result, conventionally lyophilized (S)-(+)-bis-4,4'-(1-methyl-1,2-ethanediyl)2,6piperazinedione is recommended to be stored under refrigeration.

Since the recommended doseage of ADR-529 is 1 g/Kg of patient body weight, the conventional vials occupy a large volume of refrigerator space because of the vial size. Further, the presence of even small amounts of crystalline ADR-529 in the lyophilizate will result in a product which may take up to 15 min. to dissolve when reconstituted. The pharmacist or nurse must either shake the vial for this period of time or put the reconstituted vial on a mechanical shaker and wait for the ADR-529 to go into solution. The result is that the conventional lyophilized ADR-529 is not convenient to use.

Surprisingly, the lyophilizate of the present invention does not convert from the amorphous to the crystalline form even in the presence of up to about 6% moisture when stored at room temperature for extended periods of time. The present lyophilizate almost instantaneously (2-5 sec.) dissolves when reconstituted. Arrhenius calculations based on storage of the lyophilizate of the present invention at 55° C. for four (4) weeks predicts a shelf stability for the lyophilizate of about two years at room temperature.

It is understood that changes and variations may be made from the foregoing embodiments of the present invention without departing from the spirit and scope thereof as defined in the appended claims.

What is claimed is:

1. A stable, rapidly soluble, lyophilized injectable composition containing up to about 6% moisture and capable of being stored at room temperature comprising the hydrochloric acid or sulfuric acid salt of (S)-31 (+)-bis-4,4'-(1-methyl-1,2- ethanediyl)2,6-piperazinedione or (R)—(−)-bis-4,4'-(1-methyl-1,2-ethanediyl)2,6-piperazinedione; wherein said lyophilized composition is prepared from a bulk solution comprising from about 25 mg/mL to about 40 mg/mL of said compound dissolved in hydrochloric or sulfuric acid; and wherein the pH of said bulk solution is from about 1.0 to about 2.0.

2. A composition according to claim 1 wherein said acid is hydrochloric acid.

3. A composition according to claim 2 wherein said bulk solution contains 30 mg/mL of said compound.

4. A composition according to claim 3 wherein said compound is (S)-(+)-bis-4,4'-(1-methyl-1,2-ethanediyl)2,6-piperazinedione.

5. A composition according to claim 3 wherein said compound is (R)-(-)-bis-(1-methyl-1,2-ethanediyl)2,6piperazinedione.

6. A composition according to claim 1 which dissolves in about 5 sec. upon reconstitution with a pharmaceutically acceptable diluent.

7. A composition according to claim 1 which is stable at room temperature for up to about 1½ years.

8. A composition according to claim 1 wherein said acid is sulfuric acid.

9. A sterile, intravenously injectable aqueous solution obtained, upon reconstitution of the lyophilized bulk solution is from about 1.0 to about 2.0.

10. An isotonic solution which is suitable for intravenous administration to a patient in need of treatment which has a pH of from about 3.0 to about 6.0, wherein said isotonic solution is prepared by reconstituting a lyophilizate with a pharmaceutically acceptable diluent; wherein said lyophilizate is a stable, rapidly soluble lyophilized injectable composition containing up to about 6% moisture and capable of being stored at room temperature comprising the hydrochloride or sulfate salt of (S)—(+)-bis-4,4'-(a-methyl-1,2-ethanediyl)2,6-piperazinedione or (R)—(—)-bis-4,4'-(1-methyl-1,2-ethanediyl)2,6-pierazinedione; wherein said lyophilized composition is prepared from a bulk solution comprising from about 25 mg/mL to about 40 mg/mL of said compound dissolved in hydrochloric or sulfuric acid; wherein the pH of said bulk solution is from about 1.0 to about 2.0.

11. An isotonic solution according to claim 10 wherein said acid is hydrochloric acid.

12. An isotonic solution according to claim 11 having a pH of from about 4.0 to about 5.0.

13. An isotonic solution according to claim 12 having a pH of about 5.0.

14. An isotonic solution according to claim 12 containing about 10 mg/mL of the HCl salt of (S)—(+)-bis-4,4'-(1-methyl-1,2-ethanediyl)2,6-piperazinedione.

15. An iosotonic solution according to claim 12 containing about 10 mg/mL of the HCl salt of (R)—(—)-bis-4,4'-(1-methyl-1,2-ethanediyl)2,6-piperazinedione.

* * * * *